US006877362B2

(12) United States Patent
Manaka et al.

(10) Patent No.: US 6,877,362 B2
(45) Date of Patent: Apr. 12, 2005

(54) METHOD AND DEVICE FOR EVALUATING PROCESSABILITY OF VISCOELASTIC MATERIAL, METHOD FOR SETTING CONDITION FOR PROCESSING VISCOELASTIC MATERIAL, AND DEVICE FOR PROCESSING VISCOELASTIC MATERIAL; AND METHOD FOR CONTROLLING PROCESSING OPERATION OF VISCOELASTIC MATERIAL

(75) Inventors: Masakazu Manaka, Chiba (JP); Ryoko Nonaka, Chiba (JP)

(73) Assignee: Kinugawa Rubber Ind. Co., Ltd., Chiba (JP)

( * ) Notice: Subject to any disclaimer, the term of this patent is extended or adjusted under 35 U.S.C. 154(b) by 26 days.

(21) Appl. No.: 10/641,299

(22) Filed: Aug. 15, 2003

(65) Prior Publication Data

US 2004/0148112 A1 Jul. 29, 2004

(30) Foreign Application Priority Data

Aug. 19, 2002 (JP) ....................................... 2002-237796

(51) Int. Cl.$^7$ ............................................. G01N 11/10
(52) U.S. Cl. ....................................... 73/54.41; 73/846
(58) Field of Search ............................... 73/54.41, 846; 702/34

(56) References Cited

U.S. PATENT DOCUMENTS

| 4,552,025 | A | * | 11/1985 | Barker et al. .................. 73/846 |
| 5,038,295 | A | * | 8/1991 | Husband et al. ............... 702/34 |
| 5,079,956 | A | * | 1/1992 | Burhin et al. .................. 73/846 |
| 5,287,749 | A | * | 2/1994 | Nakamura ..................... 73/808 |
| 6,408,683 | B2 | * | 6/2002 | Bahia et al. ................. 73/54.01 |

FOREIGN PATENT DOCUMENTS

| EP | 0 313 540 A1 | 4/1989 |
| EP | 1 172 641 A1 | 1/2002 |
| JP | 7-260668 A | 10/1995 |

OTHER PUBLICATIONS

Evgeny Barkanov, "Transient Response Analysis of Structures Made From Viscoelastic Materials". 1999, Int. J. Numer. Meth. Engng. 44, 393–409.*

D. T. Grubb, "Mechanical Properties of Polymers". Encyclopedia of Applied Physics, vol. 14, 1996, pp. 531–534.

* cited by examiner

*Primary Examiner*—Hezron Williams
*Assistant Examiner*—John Fitzgerald
(74) *Attorney, Agent, or Firm*—Foley & Lardner LLP

(57) ABSTRACT

A method and a device evaluate a processability of a viscoelastic material. A measuring step and means measure a complex viscosity modulus $\eta^*$ and two complex elasticity moduli $G^*1$, $G^*2$ in respective two shear ranges with different shear speeds, by the following: varying a vibration frequency and a vibration amplitude at a given temperature range, and controlling a shear stress applied to the viscoelastic material which is mixed under a given mixing condition. The shear stress causes a reactive stress. The complex viscosity modulus $\eta^*$ and the two complex elasticity moduli $G^*1$, $G^*2$ are measured based on the reactive stress. A first operation operates an apparent activation energy Ea by the following:

$$\eta^* = A \cdot \exp(Ea/RT)$$

where
T is temperature,
R is gas constant,
$\eta^*$ is complex viscosity modulus.

A second operation operates a complex elasticity modulus change ratio $G^*r$, a ratio between the two complex elasticity moduli $G^*1$, $G^*2$.

13 Claims, 9 Drawing Sheets

TEMPERATURE DEPENDENCE OF COMPLEX VISCOSITY MODULUS $\eta^*$ (STRAIN: 0.98%, VIBRATION FREQUENCY: 50 rad/s, TEMPERATURE: 60°C, 80°C, 100°C)

METHOD AND DEVICE FOR EVALUATING PROCESSABILITY OF VISCOELASTIC MATERIAL, METHOD FOR SETTING CONDITION FOR PROCESSING VISCOELASTIC MATERIAL, AND DEVICE FOR PROCESSING VISCOELASTIC MATERIAL; AND METHOD FOR CONTROLLING PROCESSING OPERATION OF VISCOELASTIC MATERIAL

BACKGROUND OF THE INVENTION

1. Field of the Invention

The present invention relates to a testing method for evaluating processability (extrudability) of a viscoelastic material (elastomer) including rubber, resin and the like.

More specifically, the present invention relates to:

a method and a device for evaluating the processability of the viscoelastic material, a method for setting a condition for processing the viscoelastic material, and a device for processing the viscoelastic material; and a method for controlling the processing operation of the viscoelastic material.

2. Description of the Related Art

A viscoelastic material such as a rubber product has quality, performance and processability which are highly sensitive to characteristics (especially, plasticity, viscosity, elasticity and the like) of its blended rubber (unvulcanized). Therefore, production, evaluation, research and development of rubber composition are in need of obtaining accurate and precise information about processability of the material (blended rubber) by measuring characteristics of the material (blended rubber).

At a mixing step for mixing the rubber in production, dispersion in the material may greatly affect processability at the next extrusion step. For reducing defect rate in processing operation, controlling the material with higher accuracy and precision is demanded recently.

Described below include measures for predicting the processability (extrudability), which measures are to be accurately and precisely evaluated:

[1] Evaluation of dispersion in extruded cross sectional shape (in other words, predicting dispersion rate of material discharge).

[2] Prediction of screw speed of extruder (in other words, predicting average material discharge).

[3] Judgment of extrudability of the material (in other words, judging whether or not the screw speed is enough for adjusting external view and cross sectional shape of extruded product).

In general, a device for measuring viscoelasticity (an important factor for rubber processing) includes what is called a Mooney viscosimeter which was released in 1934 by M. Mooney and has been widely used. Measurement method with the Mooney viscosimeter is standardized by JIS-K6300, where JIS stands for Japanese Industrial Standard.

Ordinarily, the Mooney viscosity is measured at 100° C. After preheating for 1 minute, a rotor is turned at 2 rpm. Then, after another 4 minutes, a torque about 84.6 kg·cm is defined as 100 points for a conventional Mooney viscosity $ML_{1+4}$.

Generally, the Mooney viscosimeter is widely used. With the use of the rotor, however, Mooney viscosity is measured at one point on a time axis in a broad shear speed range, thus causing difficulty in obtaining accurate and precise rubber mixed condition.

Summarizing the above, it is unlikely to obtain with the Mooney viscosimeter accurate and precise information about extrudability (extrusion discharge, extrusion dispersion and the like) which is dependent on the rubber mixed condition.

BRIEF SUMMARY OF THE INVENTION

It is an object of the present invention to provide a viscoelastic material testing method for obtaining evaluation measures for predicting processability (extrudability) of viscoelastic material, for example, blended rubber, by measuring viscoelastic characteristic of the blended rubber.

It is another object of the present invention to provide:

a method and a device for evaluating the processability of the viscoelastic material, a method for setting a condition for processing the viscoelastic material, and a device for processing the viscoelastic material; and a method for controlling the processing operation of the viscoelastic material, which methods and devices can predict with high reliability the processability of the viscoelastic material and can help produce high quality product under an optimum processing condition.

According to a first aspect of the present invention, there is provided a method for evaluating a processability of a viscoelastic material.

The method comprises the following steps:

1) a measuring step for measuring a complex viscosity modulus, by carrying out the following:

I) varying a vibration frequency and a vibration amplitude at a given temperature range, and II) controlling a shear stress applied to the viscoelastic material which is mixed under a given mixing condition, the shear stress causing a reactive stress reacting to the shear stress, the measuring step for measuring the complex viscosity modulus being based on the reactive stress; and 2) an operating step for operating an apparent activation energy of the viscoelastic material, the apparent activation energy being given by the following expression:

$$\eta^* = A \cdot \exp(Ea/RT)$$

where

T is the temperature at the measuring step,

R is a gas constant, $\eta^*$ is the complex viscosity modulus, and

Ea is the apparent activation energy which is used as a predicting value for predicting the processability of the viscoelastic material.

According to a second aspect of the present invention, there is provided a device for evaluating a processability of a viscoelastic material.

The device comprises:

1) a measuring means for measuring a complex viscosity modulus, by carrying out the following:

I) varying a vibration frequency and a vibration amplitude at a given temperature range, and II) controlling a shear stress applied to the viscoelastic material which is mixed under a given mixing condition, the shear stress causing a reactive stress reacting to the shear stress, the measuring means for measuring the complex viscosity modulus being based on the reactive stress;

2) an operating means for operating an apparent activation energy of the viscoelastic material, the apparent activation energy being given by the following expression:

$$\eta^* = A \cdot \exp(Ea/RT)$$

where
T is the temperature,
R is a gas constant,
$\eta^*$ is the complex viscosity modulus thus measured, and
Ea is the apparent activation energy;

3) a memorizing means for memorizing in advance a processable range of the apparent activation energy through a processability evaluating test, the processable range of the apparent activation energy being used for processing the viscoelastic material, where a plurality of samples mixed under substantially different mixing conditions are subjected to the processability evaluating test, the samples being made of the viscoelastic material having substantially a same blending; and 4) a comparing means for making a following comparison, so as to judge the processability of the viscoelastic material:
I) the apparent activation energy operated by the operating means, compared with the processable range of the apparent activation energy which processable range is memorized in advance by the memorizing means.

According to a third aspect of the present invention, there is provided a method for evaluating a processability of a viscoelastic material.

The method comprises the following steps:

1) a measuring step for measuring a complex viscosity modulus and two complex elasticity moduli in respective two shear ranges with different shear speeds, by carrying out the following:
I) varying a vibration frequency and a vibration amplitude at a given temperature range, and
II) controlling a shear stress applied to the viscoelastic material which is mixed under a given mixing condition, the shear stress causing a reactive stress reacting to the shear stress,
the measuring step for measuring the complex viscosity modulus and the two complex elasticity moduli being based on the reactive stress;

2) a first operating step for operating an apparent activation energy of the viscoelastic material, the apparent activation energy being given by the following expression:

$$\eta = A \cdot \exp(Ea/RT)$$

where
T is the temperature at the measuring step,
R is a gas constant,
$\eta^*$ is the complex viscosity modulus, and
Ea is the apparent activation energy which is used as a predicting value for predicting the processability of the viscoelastic material; and 3) a second operating step for operating a complex elasticity modulus change ratio which is a ratio between the thus measured two complex elasticity moduli and which is used as a predicting value for predicting the processability of the viscoelastic material.

According to a fourth aspect of the present invention, there is provided a device for evaluating a processability of a viscoelastic material.

The device comprises:

1) a measuring means for measuring a complex viscosity modulus and two complex elasticity moduli in respective two shear ranges with different shear speeds, by carrying out the following:
I) varying a vibration frequency and a vibration amplitude at a given temperature range, and
II) controlling a shear stress applied to the viscoelastic material which is mixed under a given mixing condition, the shear stress causing a reactive stress reacting to the shear stress,
the measuring means for measuring the complex viscosity modulus and the two complex elasticity moduli being based on the reactive stress;

2) a first operating means for operating an apparent activation energy (Ea) of the viscoelastic material, the apparent activation energy being given by the following expression:

$$\eta^* = A \cdot \exp(Ea/RT)$$

where
T is the temperature used by the measuring means,
R is a gas constant,
$\eta^*$ is the complex viscosity modulus, and
Ea is the apparent activation energy;

3) a second operating means for operating a complex elasticity modulus change ratio which is a ratio between the thus measured two complex elasticity moduli;

4) a memorizing means for memorizing in advance a processable range of the apparent activation energy and a processable range of the complex elasticity modulus change ratio through a processability evaluating test, the processable range of the apparent activation energy and the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending; and 5) a comparing means for making a comparison including the following, so as to judge the processability of the viscoelastic material:
I) the apparent activation energy operated by the first operating means, compared with the processable range of the apparent activation energy which processable range is memorized in advance by the memorizing means, and
II) the complex elasticity modulus change ratio operated by the second operating means, compared with the processable range of the complex elasticity modulus change ratio which processable range is memorized in advance by the memorizing means.

According to a fifth aspect of the present invention, there is provided a method for setting a condition for processing a viscoelastic material.

The method comprises the following steps:

1) a measuring step for measuring two complex elasticity moduli in respective two shear ranges with different shear speeds, by carrying out the following:
I) varying a vibration frequency and a vibration amplitude at a given temperature range, and
II) controlling a shear stress applied to the viscoelastic material which is mixed under a given mixing condition, the shear stress causing a reactive stress reacting to the shear stress, the measuring step for measuring the two complex elasticity moduli being based on the reactive stress; and 2) an operating step for operating a complex elasticity modulus change ratio which is a ratio between the thus measured two complex elasticity moduli and which is a base for setting the condition for processing the viscoelastic material.

According to a sixth aspect of the present invention, there is provided a device for processing a viscoelastic material. The device comprises:

1) a measuring means for measuring two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
   the measuring means for measuring the two complex elasticity moduli being based on the reactive stress;

2) an operating means for operating a complex elasticity modulus change ratio which is a ratio between the thus measured two complex elasticity moduli;

3) a memorizing means for memorizing in advance a processable range of the complex elasticity modulus change ratio through a processability evaluating test, the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending;

4) a comparing means for making a following comparison, so as to judge the processability of the viscoelastic material:
   I) the complex elasticity modulus change ratio operated by the operating means, compared with the processable range of the complex elasticity modulus change ratio which processable range is memorized in advance by the memorizing means;

5) a discharge operating means for operating a discharge per a processed part of a plurality of processed parts made of the viscoelastic material; and 6) a setting means for setting a condition for processing the viscoelastic material, the setting being based on the discharge of the processed part which is judged by the comparing means to have an acceptable processability, the discharge being operated by the discharge operating means.

According to a seventh aspect of the present invention, there is provided a method for controlling a processing operation of a viscoelastic material.

The method comprises the following steps:

1) a memorizing step for memorizing in advance a processable range of an apparent activation energy and a processable range of a complex elasticity modulus change ratio through a processability evaluating test, the processable range of the apparent activation energy and the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending;

2) a measuring step for measuring a complex viscosity modulus and two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
   the measuring step for measuring the complex viscosity modulus and the two complex elasticity moduli being based on the reactive stress;

3) a first operating step for operating the apparent activation energy of the viscoelastic material, the apparent activation energy being given by the following expression:

$$\eta^* = A \cdot \exp(Ea/RT)$$

where
   T is the temperature at the measuring step,
   R is a gas constant,
   $\eta^*$ is the complex viscosity modulus, and
   Ea is the apparent activation energy;

4) a second operating step for operating the complex elasticity modulus change ratio which is a ratio between the two complex elasticity moduli measured at the measuring step;

5) a first comparing step for making a following comparison, so as to judge the processability of the viscoelastic material:
   I) the apparent activation energy operated at the first operating step, compared with the processable range of the apparent activation energy which processable range is memorized at the memorizing step;

6) a second comparing step for making a following comparison, so as to judge the processability of the viscoelastic material:
   I) the complex elasticity modulus change ratio operated at the second operating step, compared with the processable range of the complex elasticity modulus change ratio which processable range is memorized at the memorizing step; and 7) a discharge operating step for operating a discharge of an extruder, the discharge being applicable to a processed part which is judged to be processable at the second comparing step, wherein,
   the extruder is so controlled as to bring about the discharge operated at the discharge operating step, and
   when the first comparing step and the second comparing step judge that the viscoelastic material is not processable, the mixing condition for the viscoelastic material is revised.

The other object(s) and feature(s) of the present invention will become understood from the following description with reference to the accompanying drawings.

DETAILED DESCRIPTION OF THE EMBODIMENT

Figure 1:
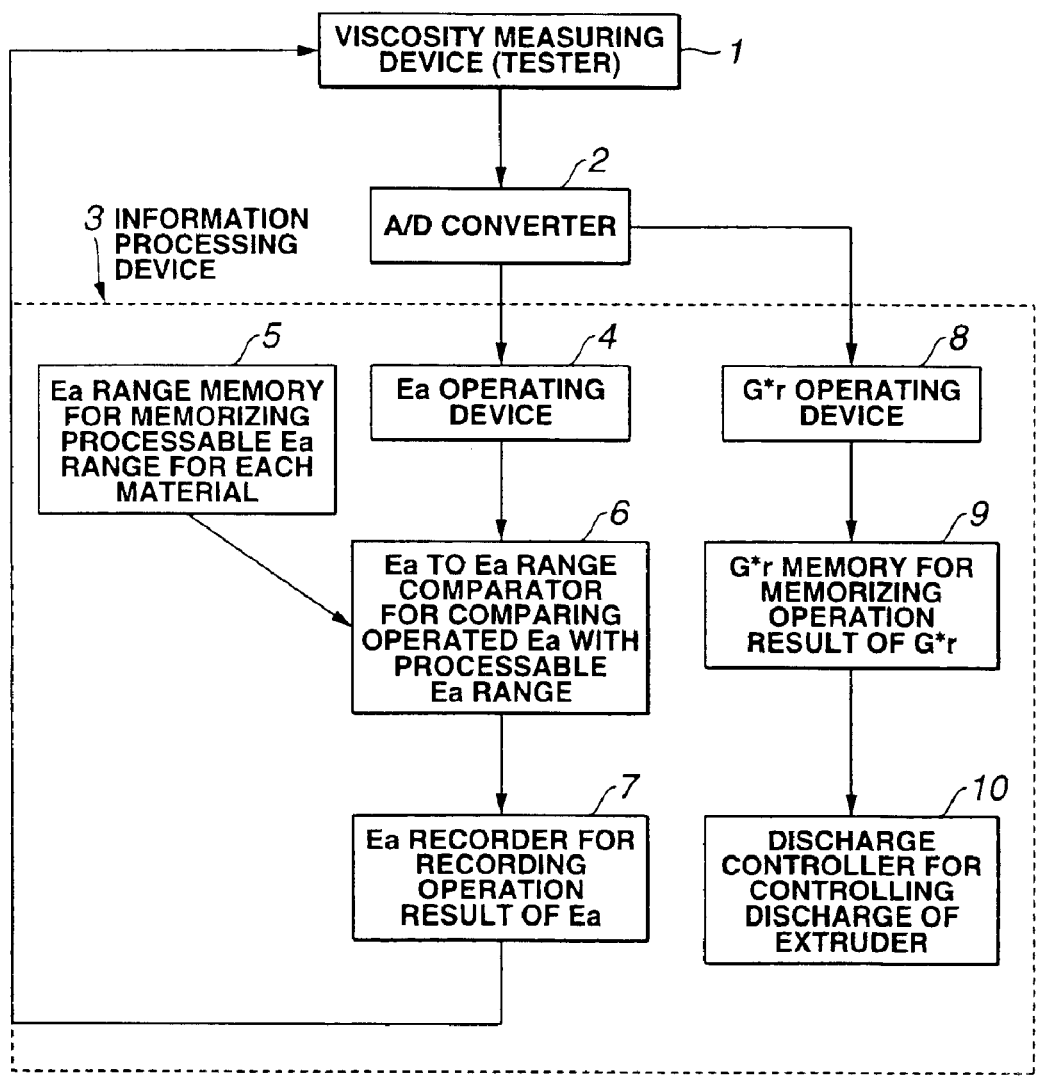
FIG. 1 is a block diagram showing that the devices according to an embodiment under the present invention are applied to a viscoelasticity testing system.

The present invention is based on the following description:

1. a complex viscosity modulus and a complex elasticity modulus which are obtainable with a known viscoelastic measuring device, and
2. Arrhenius type (Andrade equation) showing temperature dependence of the viscoelastic material:

$$\eta^* = A \cdot \exp(Ea/RT)$$

where $\eta^*$ is complex viscosity modulus, Ea is activation energy, namely, apparent activation energy of fluidity, T is temperature, and R is gas constant, so as to operate (obtain) the apparent activation energy Ea and a complex elasticity modulus change ratio G*r (r: ratio) which are used for predicting processability of the viscoelastic material.

(1) Apparent Activation Energy Ea

Carbon black blended rubber is known for the following phenomena:

Mixing carbon black blended rubber may activate mutual reaction between carbon and polymer, thus causing physical or chemical absorption or removal. With this, a rubber molecular layer is so formed as to be bound around the carbon black.

The apparent activation energy Ea may become a measure for evaluating constitution (which is variable with elapse of mixing time) of the rubber molecular layer bound around the carbon black.

More specifically, descried as below: The apparent activation energy Ea becoming greater in accordance with the elapse of mixing time shows that mobility of the rubber molecular layer bound around the carbon black is increased. Contrary to this, the apparent activation energy Ea becoming smaller in accordance with the elapse of time shows that the mobility of the rubber molecular layer bound around the carbon black is decreased.

In sum, dispersion in internal constitution of the blended rubber (namely, mobility of the rubber molecular layer bound around the carbon black) may greatly affect the following processability (extrudability).

(1-1) Surface of Extruded Product (External View)

The apparent activation energy Ea is the measure for evaluating constitutional change of the rubber molecular layer bound around the carbon black. The apparent activation energy Ea becoming excessively low may decrease mobility of the rubber molecular layer bound around the carbon black, thus causing what is called a gelation which may cause protrusions on the surface of extruded product, resulting in deteriorated external view.

(1-2) Dispersion Rate of Extrusion Discharge

The apparent activation energy Ea becoming excessively high may increase mobility of the rubber molecular layer bound around the carbon black, thus causing relatively uneven fluidity.

At the extrusion step, a screw conveys the material in order of a feed zone, a cylinder zone, a head zone and an extrusion die. In the conveying process, the material is therefore subjected to various temperature hystereses from the feed to the discharge.

The material having its blended rubber viscosity sensitive to temperature dispersion (namely, material having great apparent activation energy Ea) is likely to cause fluidity change. Thereby, the above material is likely to cause dispersion in extrusion fluidity due to slight change in extrusion environment. Actually, the extruded product by an extruder having a diameter of 70 mm or more may have greater lengthwise dispersion in discharge direction than cross sectional dispersion in swelling direction.

In sum, evaluating the apparent activation energy Ea of the blended rubber can be a measure for evaluating the surface of the extruded product and dispersion in extrusion discharge.

(2) Complex Elasticity Modulus Change Ratio G*r

Under rubber mixing condition, the complex elasticity modulus change ratio G*r is an index showing viscoelasticity characteristic which is known as Payne effect (i.e., a substantial decrease in the storage modulus of a particle-reinforced elastomer with an increase in the amplitude of mechanical oscillations). The complex elasticity modulus change ratio G*r which is relative to an electric resistance of the blended rubber can show micro-dispersion of the carbon black. The inventor of the present invention presumes that the complex elasticity modulus change ratio G*r can be useable for evaluating the processability (extrudability).

At the extrusion step, the screw conveys the material in order of the feed zone, the cylinder zone, the head zone and the extrusion die. In the conveying process, the material is therefore subjected to various shear stress hystereses. Materials having substantially the same shear speed dependence may have substantially the same fluidity in each of the zones of the extruder, thus causing substantially the same discharge. Measuring a low shear speed complex elasticity modulus G*1 and a high shear speed complex elasticity modulus G*2 for calculating the complex elasticity modulus change ratio G*r can evaluate the shear speed dependence.

At an actual extrusion step, even the same blended rubbers may have different shear speed dependencies due to lot-to-lot difference. For the above material, varying the shear speed of the extruder by adjusting the screw speed may adjust the discharge, according to the above theory. The complex elasticity modulus change ratio G*r, therefore, can be a measure for the screw speed.

Summarizing the above, the apparent activation energy Ea can be a measure for evaluating the external view of the extruded product and the dispersion in material discharge, while the complex elasticity modulus change ratio G*r can be a measure for predicting the screw speed of the extruder (predicting material discharge). Making judgment referring to the apparent activation energy Ea and the complex elasticity modulus change ratio G*r can accurately and precisely obtain the difference in mixing conditions having substantially the same blending and can evaluate the material for the extrusion.

Table 1 shows a result of a processability evaluating test with a plurality of samples including a sample A, a sample B, a sample C, a sample D, a sample E, sample F, a sample G, a sample H, a sample I, and a sample J which are mixed under substantially different mixing conditions and which are made of a viscoelastic material having substantially the same blending.

The material of each of the sample A, the sample B, the sample C, the sample D, the sample E, sample F, the sample G, the sample H, the sample I, and the sample J in Table 1 has blending of EPDM (=ethylene-propylene terpolymer) 100 phr, carbon black 170 phr, paraffin oil 70 phr, calcium carbonate heavy 20 phr, zinc flower 3 phr, stearic acid 1 phr, sulfur 1 phr, and a group consisting essentially of thiazole derivative accelerator, thiuram derivative accelerator and sulfenamide derivative accelerator 5 phr in total.

Table 2 shows various conditions (mixing method, motor speed and in-chamber temperature) for mixing samples with sealed mixer.

TABLE 1

| | Test item | Sample judged acceptable in total evaluation | | | | | Material acceptable range (Material control range) |
|---|---|---|---|---|---|---|---|
| | | A | B | C | D | E | |
| Unvulcanized rubber evaluation | Ea ($\times 10^{-1}$ kJ/mol) 60° C., 80° C., 100° C. | 104 | 104 | 98 | 92 | 92 | 92–104 |
| | G*r (%) 80° C. | 46 | 53 | 50 | 53 | 46 | 46–53 |
| | $ML_{1+4}$ 100° C. (JIS-K6300) | 59 | 43 | 50 | 45 | 61 | 43–61 |
| Extrudability evaluation | Average extrusion discharge (g/min) (16 rpm) | 480.4 | 469.0 | 475.2 | 469.1 | 480.4 | |
| | Discharge dispersion rate (%) (16 rpm) (Target: ≦2%) | 1.8 | 1.8 | 1.5 | 0.8 | 0.7 | |
| | Adjuster screw speed (rpm) | 15.6 | 16.2 | 16.0 | 16.2 | 15.6 | |
| | Cross sectional shape | OK | OK | OK | OK | OK | |
| | External view of extruded product | Good | Good | Good | Good | Good | |
| | Total evaluation of extrudability | Acceptable | Acceptable | Acceptable | Acceptable | Acceptable | |

| | Test item | Sample judged acceptable in total evaluation | | | | | Material acceptable range (Material control range) |
|---|---|---|---|---|---|---|---|
| | | F | G | H | I | J | |
| Unvulcanized rubber evaluation | Ea ($\times 10^{-1}$ kJ/mol) 60° C., 80° C., 100° C. | 119 | 115 | 80 | 115 | 115 | 92–104 |
| | G*r (%) 80° C. | 39 | 44 | 46 | 58 | 49 | 46–53 |
| | $ML_{1+4}$ 100° C. (JIS-K6300) | 64 | 59 | 59 | 40 | 50 | 43–61 |
| Extrudability evaluation | Average extrusion discharge (g/min) (16 rpm) | 485.7 | 481.4 | 480.1 | 448.0 | 475.3 | |
| | Discharge dispersion rate (%) (16 rpm) (Target: ≦2%) | 6.7 | 3.9 | 0.5 | 4.0 | 4.2 | |
| | Adjuster screw speed (rpm) | difficult to adjust (14.8) | difficult to adjust (15.3) | 15.6 | Unable to adjust | Unable to adjust | |
| | Cross sectional shape | No good | No good | OK | No good | No good | |
| | External view of extruded product | Not calendered (glossy) surface | Good | Protrusions found | Good | Good | |
| | Total evaluation of extrudability | Not acceptable | Not acceptable | Not acceptable | Not acceptable | Not acceptable | |

TABLE 2

Mixing conditions for sample A to sample J

| Sample | Mixer | Mixing method | Motor speed (rpm) | Mixing start temperature (° C.) | Mixing end temperature (° C.) |
|---|---|---|---|---|---|
| A | Meshing type | Upside down | 30 | 70 | 150 |
| B | Meshing type | Upside down | 30 | 70 | 160 |
| C | Tangential type | Conventional | 35 | 70 | 150 |
| D | Tangential type | Upside down | 25 | 70 | 150 |
| E | Tangential type | Upside down | 35 | 70 | 150 |
| F | Meshing type | Conventional | 30 | 70 | 130 |
| G | Meshing type | Conventional | 30 | 70 | 140 |
| H | Tangential type | Conventional | 30 | 70 | 130 |
| I | Meshing type | Conventional | 30 | 70 | 160 |
| J | Meshing type | Conventional | 30 | 70 | 150 |

The "Unvulcanized rubber evaluation" in Table 1 includes the apparent activation energy Ea and the complex elasticity modulus change ratio G*r which are operated in the methods according to the embodiment of the present invention. The "Unvulcanized rubber evaluation" in Table 1 also includes the conventional Moony viscosity $ML_{1+4}$.

The "Material acceptable range" of Ea and G*r in Table 1 shows a material control range of the acceptable extrudability of the evaluated blending.

The "Material acceptable range" of $ML_{1+4}$ in Table 1 shows a material control range by the conventional Mooney viscosity measurement.

<Calculate Apparent Activation Energy Ea>

A measuring device used for measuring the apparent activation energy Ea in Table 1 is RPA2000 made by ALPHA TECHNOLOGIES Inc. Evaluation with the temperature range and shear speed to be used at the extrusion is preferred. The measurement was, therefore, carried out under the following condition, according to the embodiment.

| Temperature: | 60° C., 80° C., 100° C. |
|---|---|
| Shear speed: | 0.5 s$^{-1}$ (frequency: 50 rad/s, strain modulus: 0.98%) |
| Method: | Arrhenius type (Andrade equation) |

$$\eta = A \cdot \exp(Ea/Rt) \qquad \text{Expression <1>}$$

($\eta$ is viscosity, Ea is apparent activation energy of fluidity, T is temperature, and R is gas constant).

The above measurement condition can calculate the complex viscosity modulus $\eta^*$ (viscosity $\eta$) at 60° C., 80° C., 100° C., thus calculating the apparent activation energy Ea through the expression <1>.

Figure 6:
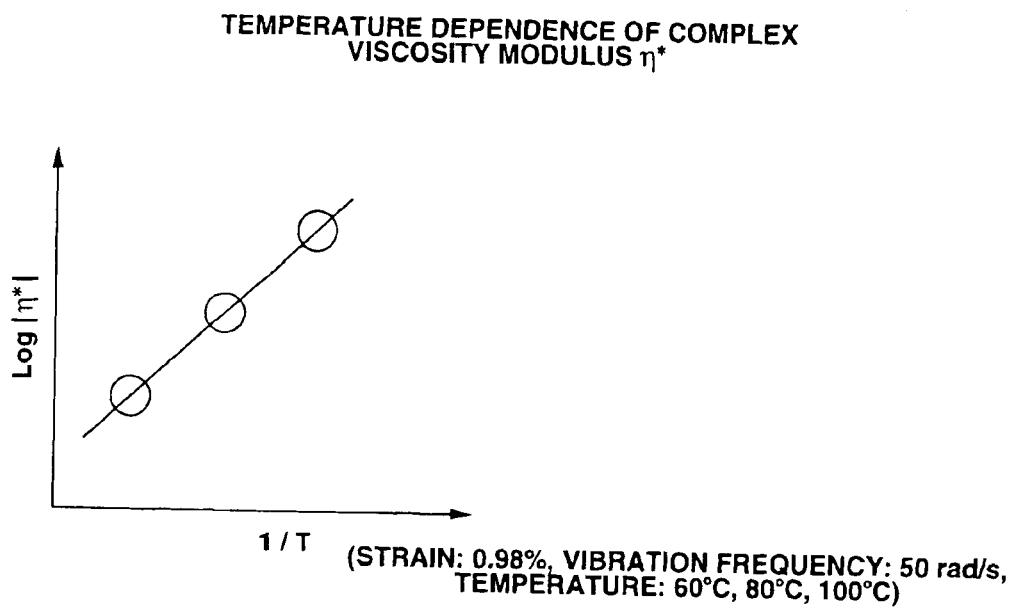
FIG. 6 shows characteristic of temperature dependence of blended rubber viscosity.

A temperature dependence of the complex viscosity modulus $\eta^*$ shows characteristic in FIG. 6.

The expression <1> can be given as follows:

$$\log(\eta^*/A) = Ea/RT$$

$$\log\eta^* - \log A = Ea/R \cdot (1/T)$$

$$\log\eta^* = Ea/R \cdot (1/T) + \log A \qquad \text{Expression <2>}$$

(Ea/R) in the expression <2> shows an inclination of the characteristic in FIG. 6.

<Calculate Complex Elasticity Modulus Change Ratio G*r>

A measuring device used for measuring the complex elasticity modulus change ratio G*r in Table 1 is the RPA2000 made by ALPHA TECHNOLOGIES Inc. Evaluation with the preferable temperature range and shear speed to be used at the extrusion is preferred. The measurement was, therefore, carried out under the following condition, according to the embodiment.

| Temperature: | 80° C. |
|---|---|
| Shear speed: | Low shear speed range 0.6 s$^{-1}$ (frequency: 100 rad/s, strain modulus: 0.98%) |
| | High shear speed range 19.8 s$^{-1}$ (frequency: 100 rad/s, strain modulus: 19.95%) |

G*1: Low shear speed complex elasticity modulus
G*2: High shear speed complex elasticity modulus $$\text{Calulating method: } G^*r\ (\%) = (G^*2/G^*1) \times 100 \qquad \text{Expression <3>}$$

Figure 7:
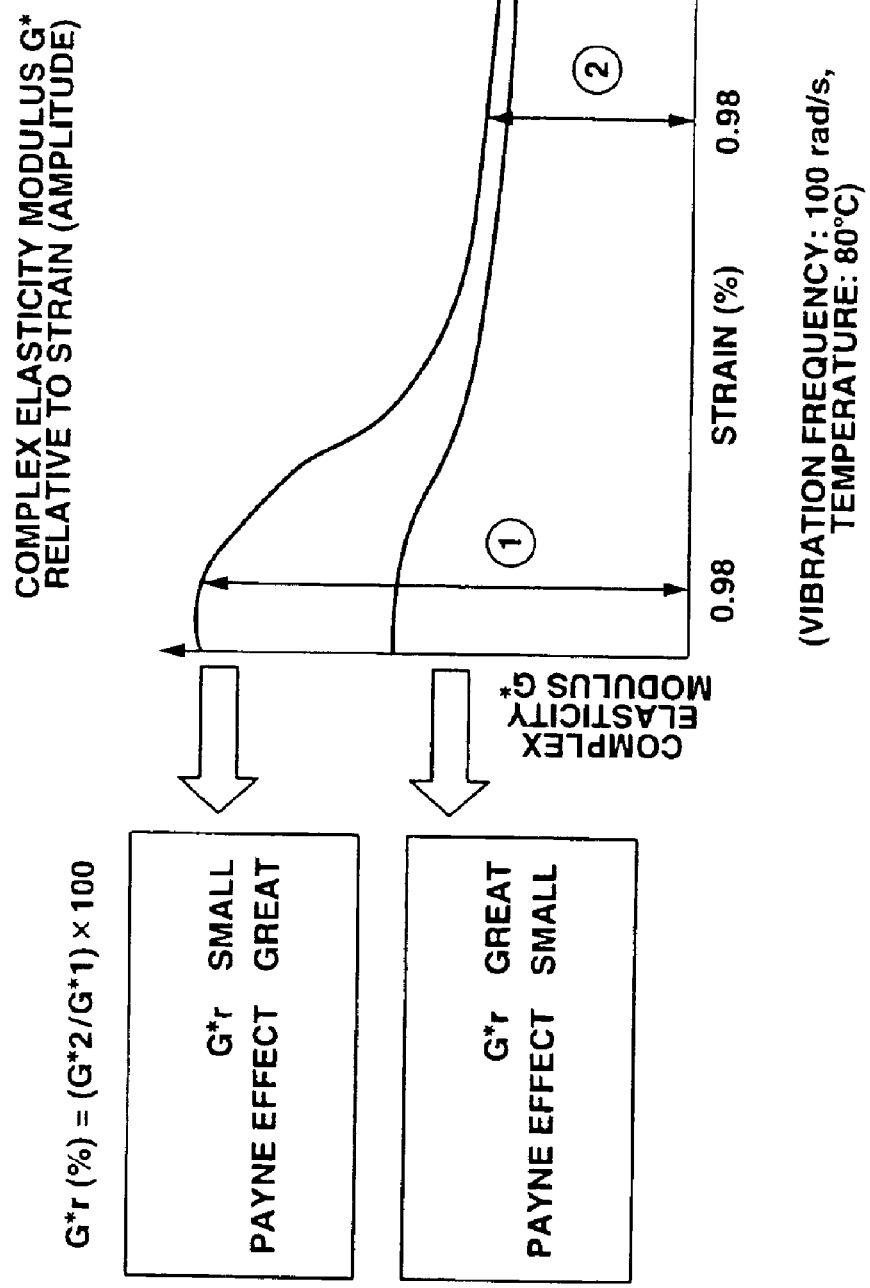
FIG. 7 shows characteristic of complex elasticity modulus G* relative to strain, for explanation of the complex elasticity modulus change ratio G*r.

FIG. 7 shows characteristic of the complex elasticity modulus G* relative to strain (amplitude). The complex elasticity modulus change ratio G*r is substantially inversely proportional to a Payne effect (i.e., a substantial decrease in the storage modulus of a particle-reinforced elastomer with an increase in the amplitude of mechanical oscillations).

"Average extrusion discharge" in the extrudability evaluation in the Table 1 can be obtained as an average discharge (sample size: n=50) for one-minute extrusion at screw speed of 16 rpm, with the extruder having diameter of 90.

"Discharge dispersion rate" in the extrudability evaluation in the Table 1 can be obtained as a discharge weight (sample size: n=50) dispersion rate for one minute at screw speed of 16 rpm, with the extruder having diameter of 90. "Discharge dispersion rate" was obtained through the following expression <4>:

$$\text{Discharge dispersion rate (\%)} = \{[\text{Maximum discharge }(g) - \text{Minimum discharge }(g)]/\text{Average discharge }(g)\} \times 100 \qquad \text{Expression <4>}$$

Figure 8:
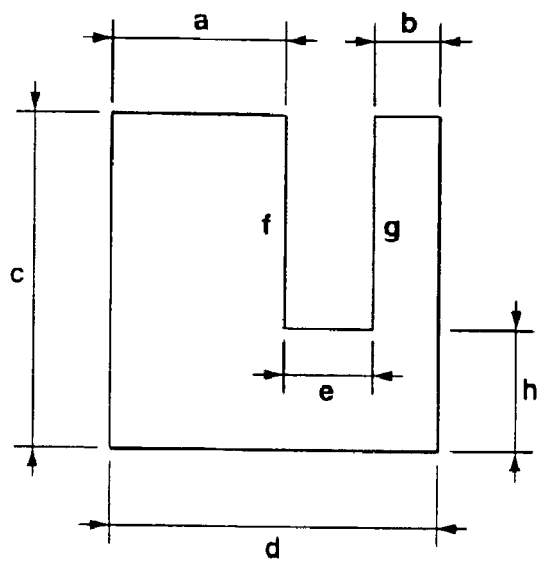
FIG. 8 shows a cross sectional shape of a part subjected to the evaluation for extrusion, according to the embodiment of the present invention.

"Cross sectional shape" in the extrudability evaluation in the Table 1 was evaluated in the following manner:

The sample C is subjected to the screw speed of 16 rpm (the extruder having diameter of φ90), so as to make an extrusion die that substantially mates with a configuration shown in FIG. 8. A voluntary sample is fed from a feed portion, so that an extruded product can be sampled 15 minutes thereafter.

In this case, the sample is to be sampled per minute for evaluation of the discharge dispersion rate (sample size: n=50). Of the above samples, a 10th sample, a 25th sample and a 50th sample are to be sampled for evaluation of the extruded cross sectional shape in the following sequential method:

Method for evaluating the cross sectional shape:
1. Extrude the sample.
2. Quench the sample (unvulcanized) for hardening, with a cold spray (an ozone spray for cooling to −30° C. or below).
3. Cut the sample.
4. Measure cross sectional shape of the sample.

Acceptance criterion:

The cross sectional shape of each of the 10th sample, the 25th sample and the 50th sample has a tolerance ±0.2 mm for dimension a to dimension h as is seen in FIG. 8. In this case, for example, a=6 mm, b=2 mm, c=11 mm, d=11 mm, e=3 mm, f=7 mm, g=7 mm, and h=4 mm.

"Adjuster screw speed" in the extrudability evaluation in Table 1 judges whether or not the screw speed is so adjustable as to cause the cross sectional shape with the dimension a to the dimension h having the tolerance ±0.2 mm. Other than the adjustable screw speed, the Table 1 also shows the screw speed that is difficult to adjust or unable to adjust. Numerically described in Table 1 shows the adjuster screw speed causing a most similar cross sectional shape.

The above "(1) Apparent activation energy Ea" and "<Calculate apparent activation energy Ea>" describe that it is "average extrusion discharge," "(1–2) Dispersion rate of extrusion discharge," and "(1—1) Surface of extruded product (external view)" that can be used for evaluating the processability in terms of the apparent activation energy Ea in Table 1.

The above "(2) Complex elasticity modulus change ratio G*r" and "<Calculate complex elasticity modulus change ratio G*r>" describe that it is "average extrusion discharge," "Adjuster screw speed," and "Cross sectional shape" that can be used for evaluating the processability in terms of the complex elasticity modulus change ratio G*r in Table 1.

In Table 1, the sample A to the sample E having the apparent activation energy Ea (obtained with the method according to the embodiment of the present invention) within the "Material acceptable range (Material control range)" are judged acceptable at the total evaluation of extrudability. Moreover, the sample A to the sample E having the apparent activation energy Ea and the complex elasticity modulus change ratio G*r within the "Material acceptable range (Material control range)" are judged acceptable at the total evaluation of extrudability.

<Conventional Mooney Viscosity $ML_{1+4}$>

The conventional Mooney viscosity $ML_{1+4}$ is to be described below. Though being within the material acceptable range (material control range) of the conventional Mooney viscosity $ML_{1+4}$, the sample G, the sample H and the sample J have at least one of deviated discharge dispersion rate, difficulty (or inability) in adjusting the cross sectional shape, and deteriorated external view of extruded product, thus rendering the conventional Mooney viscosity $ML_{1+4}$ to be useless for judging the processability of the material.

Evaluation with the conventional Mooney viscosity $ML_{1+4}$ converts a torque (stress) to the Mooney viscosity, at an ordinary temperature in the broad shear speed range (generally, about $10^{-1}$ $s^{-1}$ to about $10$ $s^{-1}$). The conventional Mooney viscosity $ML_{1+4}$, therefore, is likely to cause relatively significant difference to the mixing condition. In other words, with such unknown factors as low shear speed dispersion, dependence on shear speed (0 $s^{-1}$ to $10^2$ $s^{-1}$) applied at the extrusion, and temperature dependence, the conventional Mooney viscosity $ML_{1+4}$ cannot bring about accurate and precise information about the material.

Concerning the mixing condition of the material, an increased Mooney viscosity $ML_{1+4}$ may have difficulty in making one of or both of the following judgments:

1. Whether or not the carbon black has deteriorated dispersion.
2. Whether or not the mobility of the rubber molecular layer bound around the carbon black is responsible.

The apparent activation energy Ea and the complex elasticity modulus change ratio G*r according to the embodiment of the present invention, however, can make individual evaluations, thus judging the cause.

Concerning the extrudability dependent on the mixing condition, the increased Mooney viscosity $ML_{1+4}$ may have difficulty in making one of or all of the following judgments and the like before extrusion:

1. Whether or not the increased Mooney viscosity $ML_{1+4}$ shows deteriorated extrusion surface.
2. Whether or not the increased Mooney viscosity $ML_{1+4}$ has something to do with discharge stability.
3. Whether or not the screw speed is in need of adjustment.

The apparent activation energy Ea and the complex elasticity modulus change ratio G*r according to the embodiment of the present invention, however, can make the above judgments individually.

Described below is a method for varying en route (on the way) the cross sectional shape of the conventional extruded product. Generally, varying the extrusion screw speed can adjust the cross sectional shape with varied extrusion discharge (analogous deformation). The conventional Mooney viscosity $ML_{1+4}$ was used as a measure for predicting the extrusion speed. In other words, referring to a table showing the Mooney viscosity $ML_{1+4}$ (developed in advance) relative to the screw speed, the screw speed is adjusted based on the $ML_{1+4}$ measured before the extrusion.

The Mooney viscosity $ML_{1+4}$ evaluating the extrudability based on the one measure as described above, however, may have difficulty in making the following judgments and the like individually:

1. Whether or not the dispersion in the Mooney viscosity $ML_{1+4}$ shows the deteriorated extrusion surface.
2. Whether or not the dispersion in the Mooney viscosity $ML_{1+4}$ has something to do with the discharge stability.
3. Whether or not the screw speed is in need for adjustment.

The Mooney viscosity $ML_{1+4}$ even within the material acceptable range (the material control range) may cause defect. Thus, use of the Mooney viscosity $ML_{1+4}$ for the material control is difficult.

The evaluation with the apparent activation energy Ea, and the complex elasticity modulus change ratio G*r according to the embodiment of the present invention can bring about accurate and precise information about the extrudability. In other words, eliminating the need for extrusion of the product having an actual shape, the apparent activation energy Ea and the complex elasticity modulus change ratio G*r can carry out the accurate and precise evaluation in a short time.

Figure 9:
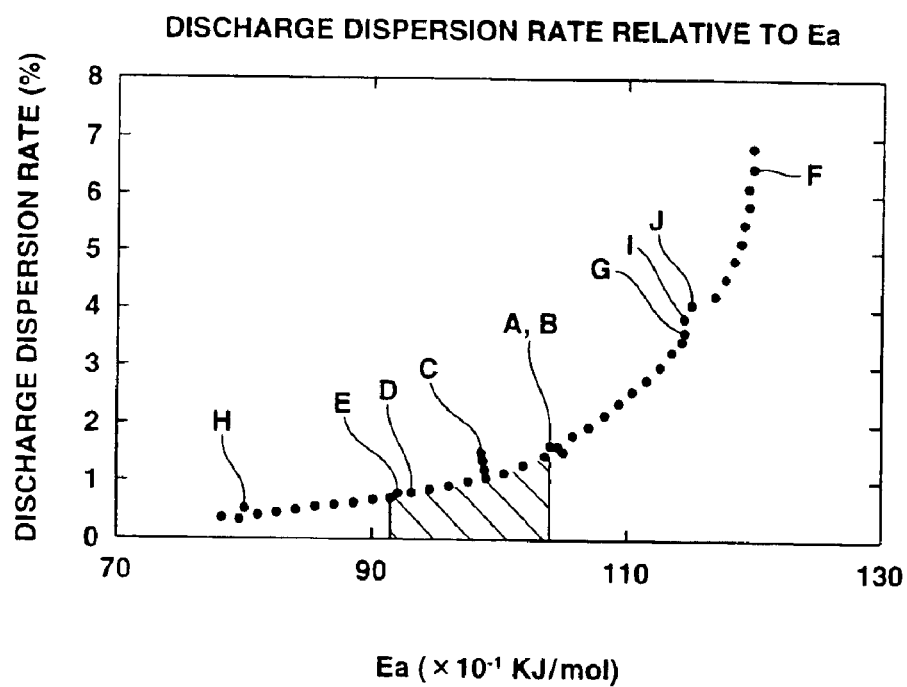
FIG. 9 shows a graph of discharge dispersion rate relative to the apparent activation energy Ea, for evaluating extrudability with the device and method according to the embodiment of the present invention applied to a plurality of samples which are mixed under substantially different mixing conditions.

FIG. 9 shows a graph of discharge dispersion rate relative to the apparent activation energy Ea of each of the sample A to the sample J in Table. 1.

Figure 10:
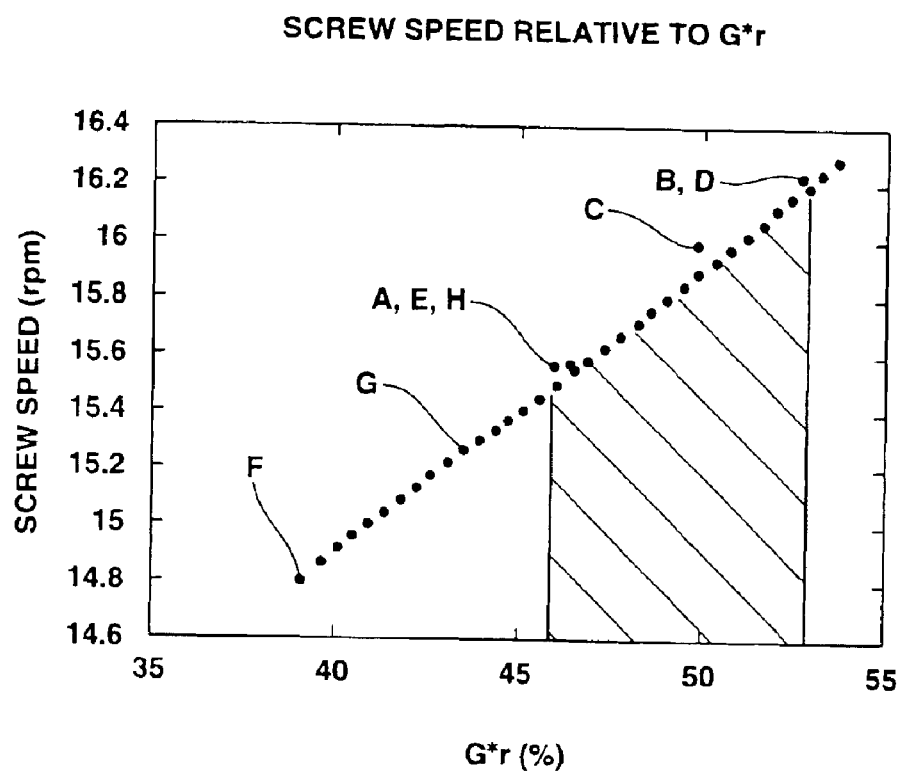
FIG. 10 shows a graph of screw speed relative to the complex elasticity modulus change ratio G*r, for evaluating extrudability with the device and method according to the embodiment of the present invention applied to the plurality of the samples which are mixed under substantially different mixing conditions.

FIG. 10 shows a graph of screw speed relative to the complex elasticity modulus change ratio G*r of each of the sample A to the sample J in Table. 1.

<Exemplary Embodiment>

Hereinafter described is an exemplary embodiment under the present invention.

According to the exemplary embodiment, a viscoelasticity testing system for carrying out the methods under the present invention is constituted in a manner shown in FIG. 1.

There is provided a viscoelasticity measuring device 1 including a sample chamber, a driving mechanism and a converter. The sample chamber houses a viscoelasticity sample for measurement and is temperature-controlled. Controlling vibration frequency and vibration amplitude (strain), the driving mechanism applies a shear stress to the sample. The converter detects a reactive torque (stress) for conversion into an electric signal.

There is provided an A/D converter 2 for converting an analogue signal {which corresponds to the reactive torque (stress) outputted from the viscoelasticity measuring device 1} into a digital signal.

There is provided an information processing device 3 for recording the signal from the A/D converter 2. After measurement, the information processing device 3 reads out the memorized data, to thereby carry out processing.

In the information processing device 3, there is provided an Ea operating device 4 which operates the complex viscosity modulus $\eta^*$ based on the data {which corresponds to the reactive torque (stress)} memorizing output from the A/D converter 2. Then, the Ea operating device 4 operates the apparent activation energy Ea through the expression <1> with the thus operated complex viscosity modulus $\eta^*$.

There is provided an Ea range memory 5 for memorizing a processable Ea range (for example, the material acceptable range in Table 1) of each material.

There is provided an Ea to Ea range comparator 6 for comparing the Ea (operated by the Ea operating device 4) with the Ea range (memorized by the Ea range memory 5). With the above comparison, the Ea to Ea range comparator 6 can judge extrudability characteristics including the discharge dispersion, the external view and the like.

There is provided an Ea recorder 7 for recording operation result with the Ea to Ea range comparator 6.

There is provided a G*r operating device 8. From the data {which corresponds to the reactive torque (stress)} memorizing the output from the A/D converter 2, the G*r operating device 8 operates the complex elasticity modulus change ratio G*r through the expression <3>.

There is provided a G*r memory 9 for memorizing operation result by the G*r operating device 8.

There is provided a discharge controller 10 for controlling the extrusion discharge based on the data memorized by the G*r memory 9.

Figure 2:
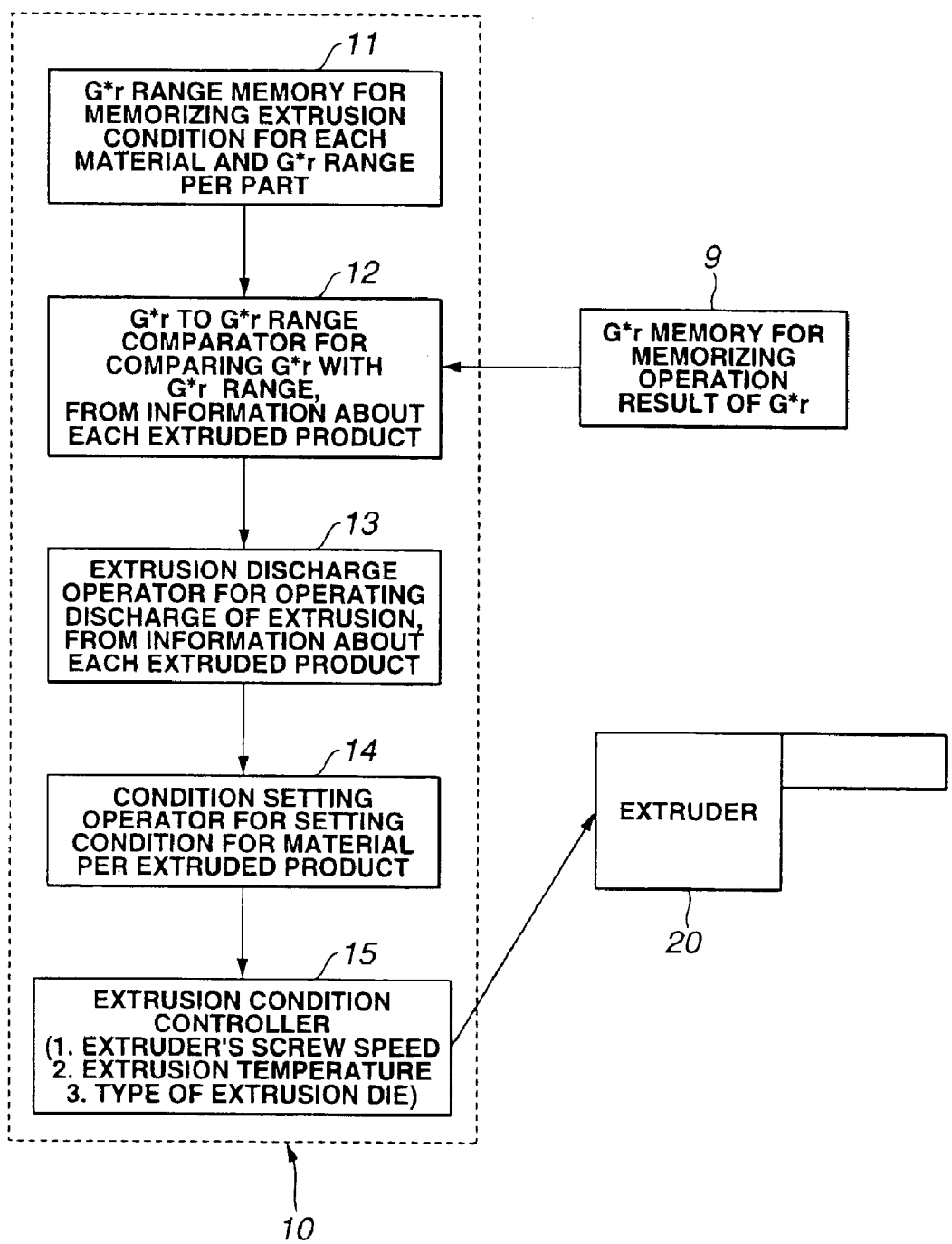
FIG. 2 is a block diagram showing constitutional elements in FIG. 1.

FIG. 2 shows an example of a constitution of the discharge controller 10.

There is provided a G*r range memory 11 for memorizing the following:
1. Extrusion condition of each material.
2. G*r range of material per part.

There is provided a G*r to G*r range comparator 12. From the information about each processed part, the G*r to G*r range comparator 12 may compare the processable G*r range with the G*r (memorized by the G*r memory 9).

There is provided an extrusion discharge operator 13 for operating (calculating) the extrusion discharge based on the information about each processability.

There is provided a condition setting operator 14 for setting condition of the material per processed part.

There is provided an extrusion condition controller 15 for controlling an extruder 20, by determining the extruding screw speed, extrusion temperature, extrusion die type and the like which are under the condition set by the condition setting operator 14.

<Flow Chart of Judging Apparent Activation Energy Ea>

Figure 3:
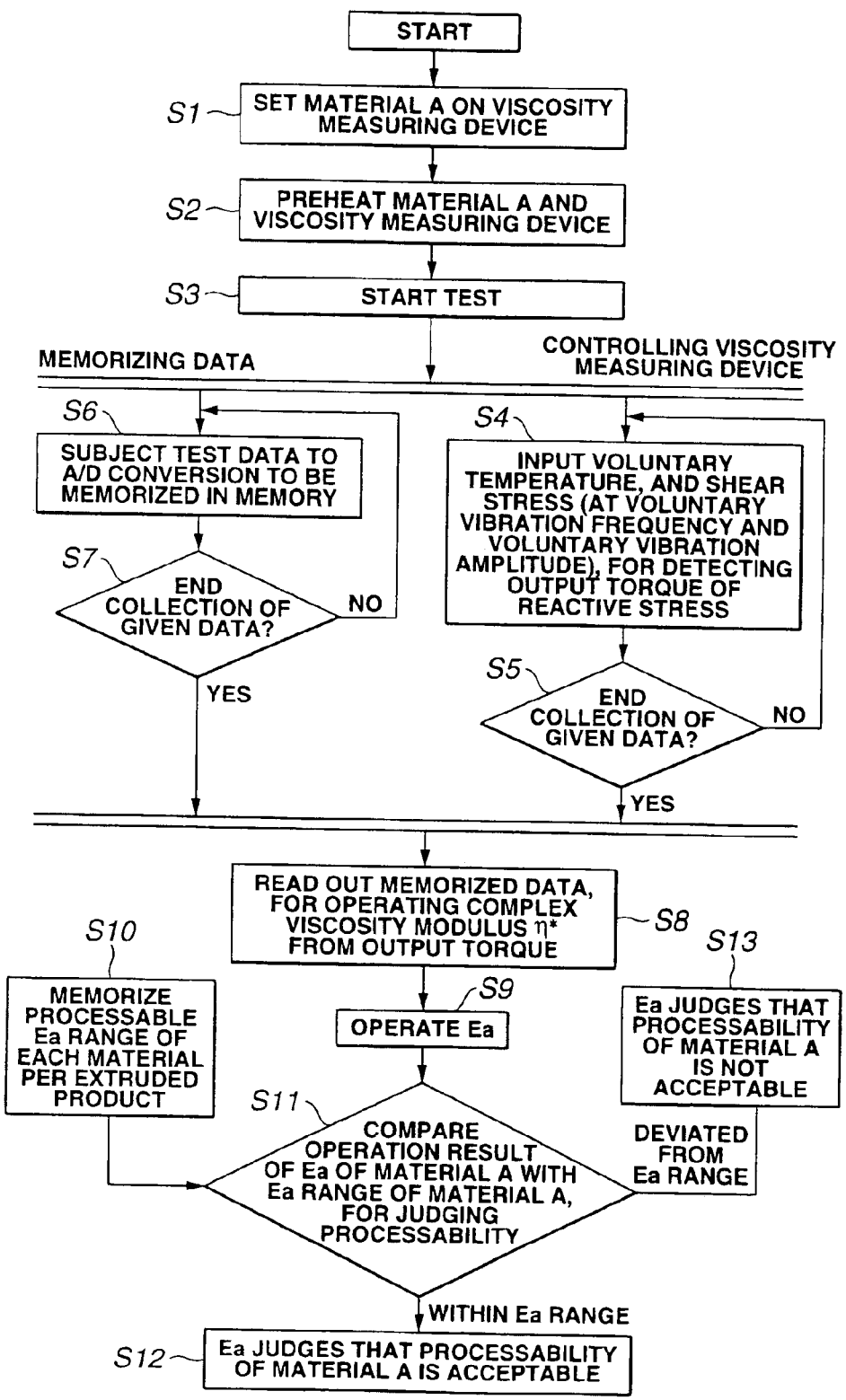
FIG. 3 is a flow chart showing an exemplary process for evaluating processability with an apparent activation energy Ea.

FIG. 3 shows an exemplary flow chart of judging the apparent activation energy Ea, according to the embodiment of the present invention.

The flow chart in FIG. 3 may be carried out as a program of CPU of the viscoelasticity testing system in FIG. 1 and FIG. 2.

[Step 1]
In FIG. 3, the material A is set for preparation on the viscoelasticity measuring device 1 (tester) in FIG. 1.

[Step 2]
The material A and the viscoelasticity measuring device 1 are preheated.

[Step 3]
The test is started.

Then, the following group 1 (including step 4 and step 5) on the right side and a group 2 (including step 6 and step 7) on the left side are carried out substantially in parallel.

[Step 4 of Group 1]
With the viscoelasticity measuring device 1 in FIG. 1: The material A is housed in the test chamber at a voluntary temperature, and a shear stress having a voluntary vibration frequency and a voluntary vibration amplitude (strain) is inputted to the material A, so as to detect the reactive torque (stress) outputted. The operation at step 4 is to be continued until a given data is obtained.

[Step 5 of Group 1]
After obtaining the given data, the routine ends the operation at step 4.

[Step 6 of Group 2]
The thus obtained data is converted (A/D), to be memorized by a memory (not shown in FIG. 1) which is included in the A/D converter 2. The operation at step 6 is to be continued until a given data is obtained.

[Step 7 of Group 2]
After obtaining the given data, the routine ends the operation at step 6.

[Step 8]
After ending operations at step 5 and step 7, the routine reads out the data (memorized at step 6) so as to calculate the complex viscosity modulus $\eta^*$ from the output torque (stress).

[Step 9]
The routine operates the apparent activation energy Ea through the expression <1>.

[Step 10]
On the other hand, the routine memorizes the processable Ea range of each material per part.

[Step 11]
The routine compares the Ea of the material A (operation result at step 9) with the processable Ea range of the material A, thus judging the processability.

[Step 12]
With the Ea of the material A within the processable Ea range at step 11, the routine judges that the processability of the material A is acceptable.

[Step 13]
With the Ea of the material A deviated from the processable Ea range at step 11, the routine judges that the processability of the material A is not acceptable.

<Flow Chart of Judging Complex Elasticity Modulus Change Ratio G*r>

Figure 4:
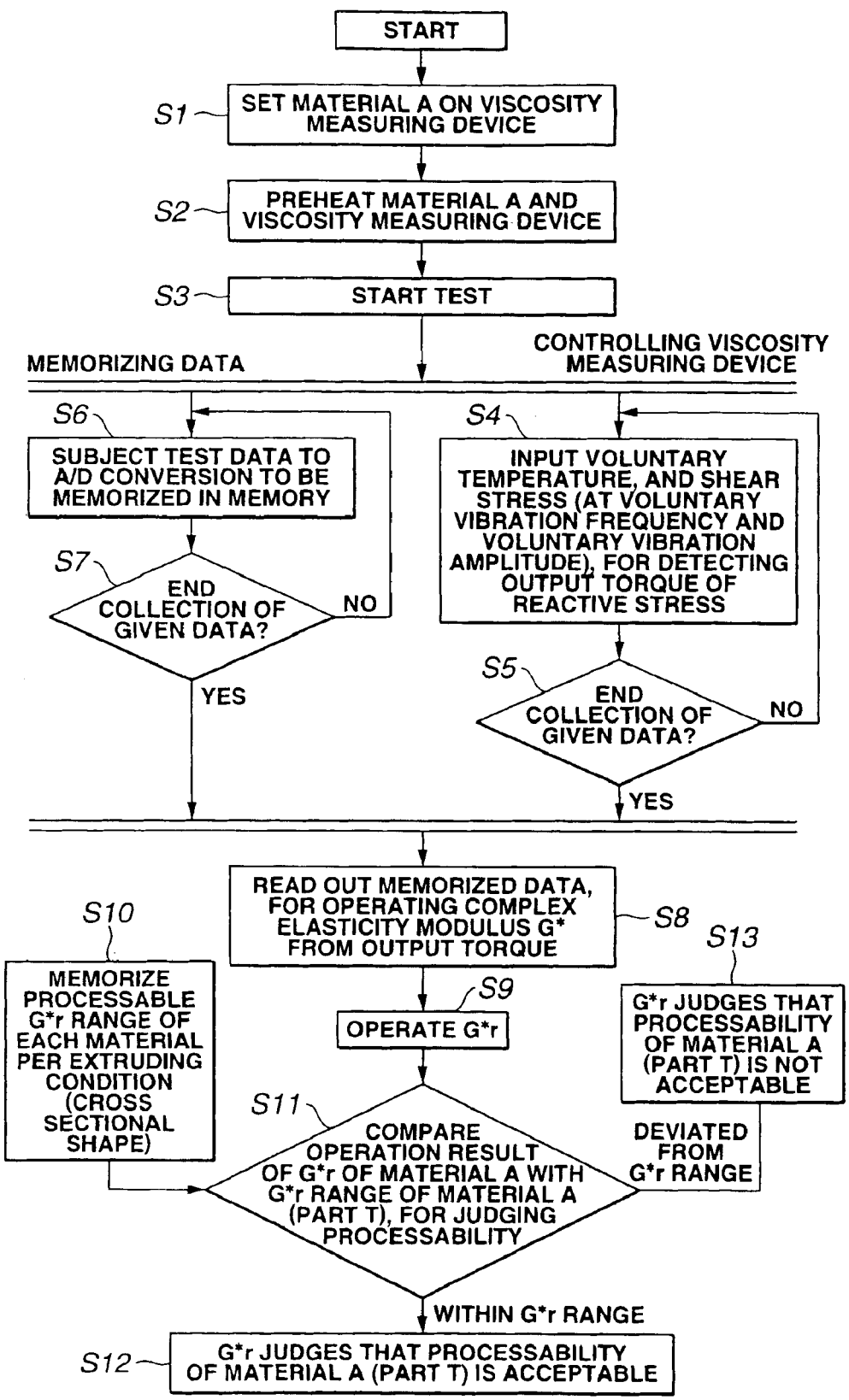
FIG. 4 is a flow chart showing an exemplary process for evaluating processability with a complex elasticity modulus change ratio G*r.

FIG. 4 shows an exemplary flow chart of judging the complex elasticity modulus change ratio G*r, according to the embodiment of the present invention.

The flow chart in FIG. 4 may be carried out as the program of the CPU of the viscoelasticity testing system in FIG. 1 and FIG. 2.

[Step 1]
In FIG. 4, the material A is set for preparation on the viscoelasticity measuring device 1 (tester) in FIG. 1.

[Step 2]
The material A and the viscoelasticity measuring device 1 are preheated.

[Step 3]
The test is started.

Then, the following group 1 (including step 4 and step 5) on the right side and a group 2 (including step 6 and step 7) on the left side are carried out substantially in parallel.

[Step 4 of Group 1]

With the viscoelasticity measuring device 1 in FIG. 1: The material A is housed in the test chamber at a voluntary temperature, and a shear stress having a voluntary vibration frequency and a voluntary vibration amplitude (strain) is inputted to the material A, so as to detect the reactive torque (stress) outputted. The operation at step 4 is to be continued until a given data is obtained.

[Step 5 of Group 1]

After obtaining the given data, the routine ends the operation at step 4.

[Step 6 of Group 2]

The thus obtained data is converted (A/D), to be memorized by the memory (not shown in FIG. 1) which is included in the A/D converter 2. The operation at step 6 is to be continued until a given data is obtained.

[Step 7 of Group 2]

After obtaining the given data, the routine ends the operation at step 6.

[Step 8]

After ending operations at step 5 and step 7, the routine reads out the data (memorized at step 6) so as to calculate the complex elasticity modulus G* from the output torque (stress).

[Step 9]

The routine operates the complex elasticity modulus change ratio G*r through the expression <3>.

[Step 10]

On the other hand, the routine memorizes the processable G*r range of each material per part, more specifically, per part's processing condition including the cross sectional shape.

[Step 11]

The routine compares the G*r of the material A (operation result at step 9) with the processable G*r range of the material A (part T), thus judging the processability.

[Step 12]

With the G*r of the material A within the processable G*r range at step 11, the routine judges that the processability of the material A (part T) is acceptable.

[Step 13]

With the G*r of the material A deviated from the processable G*r range at step 11, the routine judges that the processability of the material A (part T) is not acceptable.

<Flow Chart of Processing Control Chart (Production Control Chart)>

Figure 5:
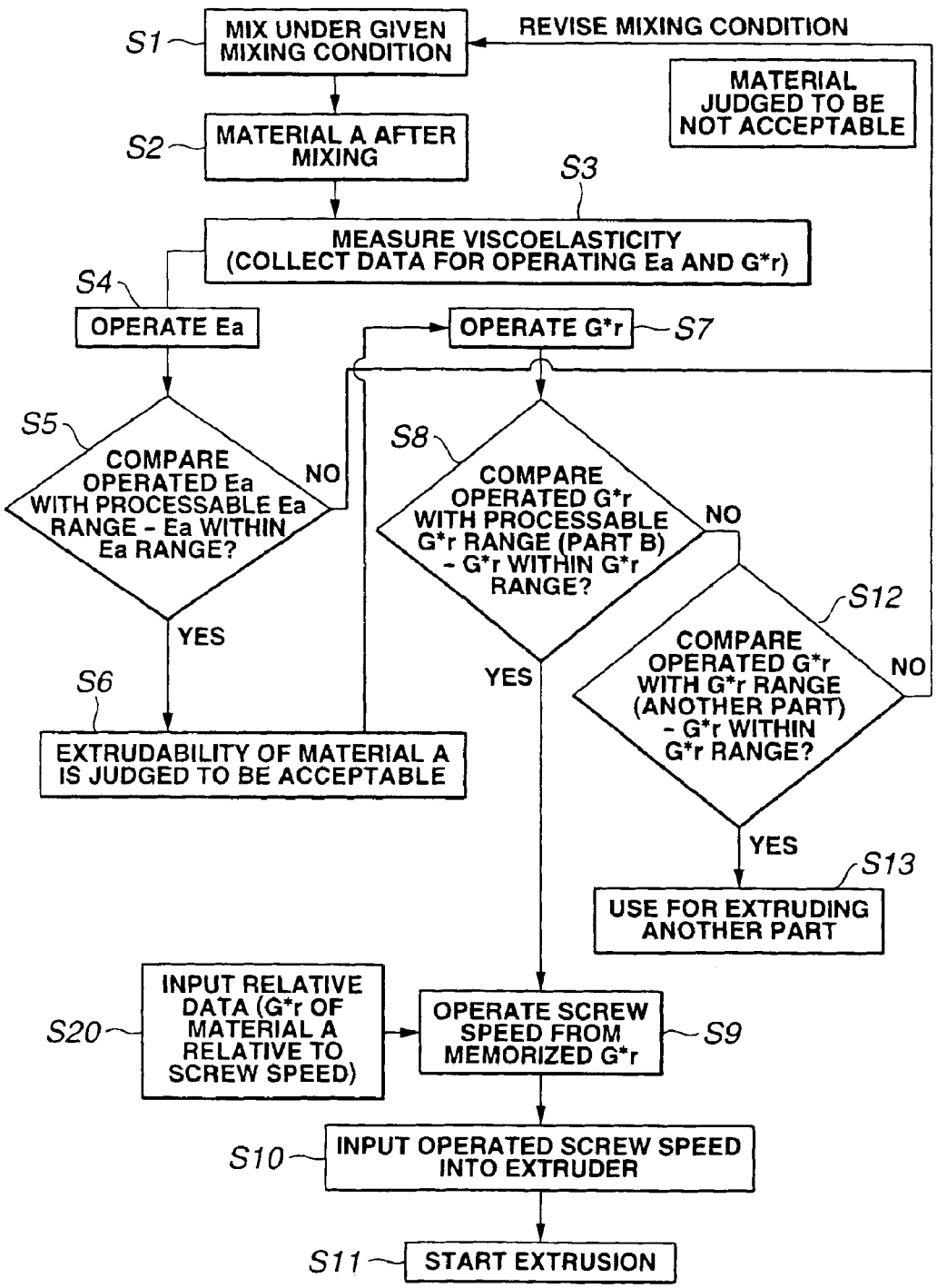
FIG. 5 is a flow chart showing an exemplary process for controlling production (processing operation) by evaluating processability with the apparent activation energy Ea and the complex elasticity modulus change ratio G*r.

FIG. 5 shows a flow chart of a processing control chart (production control chart), according to the exemplary embodiment of the present invention.

[Step 1]

The routine carries out the mixing under the set mixing condition.

[Step 2]

The routine obtains the material A after the mixing.

[Step 3]

The routine measures viscoelasticity by using, for example, the viscoelasticity measuring device 1 in FIG. 1, so as to obtain the data necessary for operating the apparent activation energy Ea and the complex elasticity modulus change ratio G*r.

[Step 4]

The routine operates the apparent activation energy Ea.

[Step 5]

The routine compares the Ea (operated at step 4) of the material A with the processable Ea range (memorized in advance) of the material A.

If Yes at step 5 (namely, Ea is within Ea range), the routine moves to the subsequent step 6.

[Step 6]

The routine judges that the extrudability of the material A is acceptable.

[Step 7]

The routine operates the complex elasticity modulus change ratio G*r.

[Step 8]

The routine makes the following comparison:

the operated G*r of the material A–operation result at step 7, compared with the processable G*r range (which is memorized in advance) of the material A (part B).

[Step 9]

With the G*r of the material A within the processable G*r range of the material A (part B) at step 8, the routine operates the screw speed (namely, discharge), referring to data of the material A. Hereinabove, the data is developed and memorized in advance at step 20, and is on the complex elasticity modulus change ratio G*r relative to the screw speed.

[step 10]

The routine inputs the thus operated screw speed into the extruder.

[Step 11]

The routine starts the extrusion.

[Step 12]

With the G*r of the material A deviated from the processable G*r range of the material A (part B) at step 8, the routine makes the following comparison:

the operated G*r of the material A–operation result at step 7, compared with the G*r range of the material A (another part).

If Yes at step 12 {namely, G*r of the material A is within the G*r range of the material A (another part)}, the routine moves to the subsequent step 13.

[Step 13]

The routine uses the material A for extrusion of the material A (another part).

If No at step 5 or at step 12, the routine judges that the material is not acceptable, and therefore revises the mixing condition.

In sum, the apparent activation energy Ea and the complex elasticity modulus change ratio G*r which achieve accurate and precise processability evaluation can be used for the production control for producing processed parts made of the viscoelastic material.

At step 20, memorizing in advance the data on the complex elasticity modulus change ratio G*r relative to the screw speed can omit operating the screw speed from time to time, thus shortening time for one processing cycle.

Although the present invention has been described above by reference to a certain embodiment, the present invention is not limited to the embodiment described above. Modifications and dispersions of the embodiment described above will occur to those skilled in the art, in light of the above teachings.

The device for evaluating processability of the viscoelastic material or the device for processing the viscoelastic material is not limited to the one shown in FIG. 1 and FIG. 2 using the apparent activation energy Ea and the complex elasticity modulus change ratio G*r. The device can use only one of the apparent activation energy Ea and the complex elasticity modulus change ratio G*r.

The viscoelasticity measuring device 1 in FIG. 1 can collect data (including the complex viscosity modulus $\eta^*$ and the complex elasticity modulus G*), for example, at room temperature to 230° C.

According to the embodiment of the present invention, measurement of the apparent activation energy Ea specifies the temperature of 60° C., 80° C. and 100° C. The present invention is, however, not limited to the above temperatures. Other temperature is acceptable for measurement of the apparent activation energy Ea.

According to the embodiment of the present invention, the shear speeds for obtaining the complex elasticity modulus change ratio G*r includes the low shear speed $0.6 \text{ s}^{-1}$ and the high shear speed $19.8 \text{ s}^{-1}$. The present invention is, however, not limited to the above two shear speeds. Other shear speed is acceptable.

An excessively high or low apparent activation energy Ea (namely, worsened Ea) may eventually deteriorate the external view of the extruded product. The apparent activation energy Ea is, therefore, preferably to be set in advance in such a manner that the discharge dispersion may not affect the extrudability, thus achieving more accurate and precise quality control of the material.

The applicability of the embodiment of the present invention is not limited to the evaluation or production of the rubber composition. The embodiment of the present invention is also applicable to the resin, bringing about substantially the same effect and operation.

This application is based on a prior Japanese Patent Application No. P2002-237796 (filed on Aug. 19, 2002 in Japan). The entire contents of the Japanese Patent Application No. P2002-237796 from which priority is claimed is incorporated herein by reference, in order to take some protection against mis-translation or omitted portions.

The scope of the present invention is defined with reference to the following claims.

What is claimed is:

1. A method for evaluating a processability of a viscoelastic material, comprising the following steps:
 1) a measuring step for measuring a complex viscosity modulus, by carrying out the following:
  I) varying a vibration frequency and a vibration amplitude at a given temperature range, and
  II) controlling a shear stress applied to the viscoelastic material which is mixed under a given mixing condition, the shear stress causing a reactive stress reacting to the shear stress,
  the measuring step for measuring the complex viscosity modulus being based on the reactive stress; and
 2) an operating step for operating an apparent activation energy of the viscoelastic material, the apparent activation energy being given by the following expression:

$$\eta^* = A \cdot \exp(Ea/RT)$$

where
 T is the temperature at the measuring step,
 R is a gas constant,
 $\eta^*$ is the complex viscosity modulus, and
 Ea is the apparent activation energy which is used as a predicting value for predicting the processability of the viscoelastic material.

2. The method for evaluating the processability of the viscoelastic material, as claimed in claim 1, wherein
 a plurality of samples mixed under substantially different mixing conditions are subjected to a processability evaluating test, the samples being made of the viscoelastic material having substantially a same blending, and
 through the processability evaluating test, a processable range of the apparent activation energy is memorized in advance, the processable range of the apparent activation energy being used for processing the viscoelastic material.

3. The method for evaluating the processability of the viscoelastic material, as claimed in claim 1, wherein
 the processability of the viscoelastic material includes:
 1) an average of an extrusion discharge,
 2) a dispersion rate of the extrusion discharge, and
 3) an external view of an extruded product.

4. A device for evaluating a processability of a viscoelastic material, comprising:
 1) a measuring means for measuring a complex viscosity modulus, by carrying out the following:
  I) varying a vibration frequency and a vibration amplitude at a given temperature range, and
  II) controlling a shear stress applied to the viscoelastic material which is mixed under a given mixing condition, the shear stress causing a reactive stress reacting to the shear stress,
  the measuring means for measuring the complex viscosity modulus being based on the reactive stress;
 2) an operating means for operating an apparent activation energy of the viscoelastic material, the apparent activation energy being given by the following expression:

$$\eta^* = A \cdot \exp(Ea/RT)$$

where
 T is the temperature,
 R is a gas constant,
 $\eta^*$ is the complex viscosity modulus thus measured, and
 Ea is the apparent activation energy;
 3) a memorizing means for memorizing in advance a processable range of the apparent activation energy through a processability evaluating test, the processable range of the apparent activation energy being used for processing the viscoelastic material, where a plurality of samples mixed under substantially different mixing conditions are subjected to the processability evaluating test, the samples being made of the viscoelastic material having substantially a same blending; and
 4) a comparing means for making a following comparison, so as to judge the processability of the viscoelastic material:
  I) the apparent activation energy operated by the operating means, compared with the processable range of the apparent activation energy which processable range is memorized in advance by the memorizing means.

5. A method for evaluating a processability of a viscoelastic material, comprising the following steps:
 1) a measuring step for measuring a complex viscosity modulus and two complex elasticity moduli in respective two shear ranges with different shear speeds, by carrying out the following:
  I) varying a vibration frequency and a vibration amplitude at a given temperature range, and
  II) controlling a shear stress applied to the viscoelastic material which is mixed under a given mixing condition, the shear stress causing a reactive stress reacting to the shear stress,
  the measuring step for measuring the complex viscosity modulus and the two complex elasticity moduli being based on the reactive stress;
 2) a first operating step for operating an apparent activation energy of the viscoelastic material, the apparent activation energy being given by the following expression:

$$\eta^* = A \cdot \exp(Ea/RT)$$

where
T is the temperature at the measuring step,
R is a gas constant,
$\eta^*$ is the complex viscosity modulus, and
Ea is the apparent activation energy which is used as a predicting value for predicting the processability of the viscoelastic material; and 3) a second operating step for operating a complex elasticity modulus change ratio which is a ratio between the thus measured two complex elasticity moduli and which is used as a predicting value for predicting the processability of the viscoelastic material.

6. The method for evaluating the processability of the viscoelastic material, as claimed in claim 5, wherein
a plurality of samples mixed under substantially different mixing conditions are subjected to a processability evaluating test under a given processing condition, the samples being made of the viscoelastic material having substantially a same blending,
through the processability evaluating test, a processable range of the apparent activation energy and a processable range of the complex elasticity modulus change ratio are memorized in advance, the processable range of the apparent activation energy and the processable range of the complex elasticity modulus change ratio being used for processing the viscoelastic material.

7. The method for evaluating the processability of the viscoelastic material, as claimed in claim 5, wherein the processability includes:
1) an average of an extrusion discharge,
2) a screw speed of an extruder, for bringing about an allowable tolerance to a dimension of a cross sectional shape of a processed part, and
3) the cross sectional shape of the processed part.

8. A device for evaluating a processability of a viscoelastic material, comprising:
1) a measuring means for measuring a complex viscosity modulus and two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
   the measuring means for measuring the complex viscosity modulus and the two complex elasticity moduli being based on the reactive stress;
2) a first operating means for operating an apparent activation energy of the viscoelastic material, the apparent activation energy being given by the following expression:

$$\eta^* = A \cdot \exp(Ea/RT)$$

where
T is the temperature used by the measuring means,
R is a gas constant,
$\eta^*$ is the complex viscosity modulus, and
Ea is the apparent activation energy;
3) a second operating means for operating a complex elasticity modulus change ratio which is a ratio between the thus measured two complex elasticity moduli;

4) a memorizing means for memorizing in advance a processable range of the apparent activation energy and a processable range of the complex elasticity modulus change ratio through a processability evaluating test, the processable range of the apparent activation energy and the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending; and 5) a comparing means for making a comparison including the following, so as to judge the processability of the viscoelastic material:
   I) the apparent activation energy operated by the first operating means, compared with the processable range of the apparent activation energy which processable range is memorized in advance by the memorizing means, and
   II) the complex elasticity modulus change ratio operated by the second operating means, compared with the processable range of the complex elasticity modulus change ratio which processable range is memorized in advance by the memorizing means.

9. A method for setting a condition for processing a viscoelastic material, comprising the following steps:
1) a measuring step for measuring two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
   the measuring step for measuring the two complex elasticity moduli being based on the reactive stress; and
2) an operating step for operating a complex elasticity modulus change ratio which is a ratio between the thus measured two complex elasticity moduli and which is a base for setting the condition for processing the viscoelastic material.

10. The method for setting the condition for processing the viscoelastic material, as claimed in claim 9, wherein
a plurality of samples mixed under substantially different mixing conditions are subjected to a processability evaluating test under a given processing condition, the samples being made of the viscoelastic material having substantially a same blending,
through the processability evaluating test, a processable range of the complex elasticity modulus change ratio are memorized in advance, the processable range of the complex elasticity modulus change ratio being used for processing the viscoelastic material.

11. A device for processing a viscoelastic material, comprising:
1) a measuring means for measuring two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
the measuring means for measuring the two complex elasticity moduli being based on the reactive stress;

2) an operating means for operating a complex elasticity modulus change ratio which is a ratio between the thus measured two complex elasticity moduli;

3) a memorizing means for memorizing in advance a processable range of the complex elasticity modulus change ratio through a processability evaluating test, the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending;

4) a comparing means for making a following comparison, so as to judge the processability of the viscoelastic material:
   I) the complex elasticity modulus change ratio operated by the operating means, compared with the processable range of the complex elasticity modulus change ratio which processable range is memorized in advance by the memorizing means;

5) a discharge operating means for operating a discharge per a processed part of a plurality of processed parts made of the viscoelastic material; and 6) a setting means for setting a condition for processing the viscoelastic material, the setting being based on the discharge of the processed part which is judged by the comparing means to have an acceptable processability, the discharge being operated by the discharge operating means.

12. A method for controlling a processing operation of a viscoelastic material, comprising the following steps:

1) a memorizing step for memorizing in advance a processable range of an apparent activation energy and a processable range of a complex elasticity modulus change ratio through a processability evaluating test, the processable range of the apparent activation energy and the processable range of the complex elasticity modulus change ratio being used for processing the viscoelastic material, where a plurality of samples mixed under substantially different mixing conditions are subjected to the processability evaluating test under a given processing condition, the samples being made of the viscoelastic material having substantially a same blending;

2) a measuring step for measuring a complex viscosity modulus and two complex elasticity moduli in respective two shear ranges with different shear speeds, by carrying out the following:
   I) varying a vibration frequency and a vibration amplitude at a given temperature range, and
   II) controlling a shear stress applied to the viscoelastic material which is mixed under a given mixing condition, the shear stress causing a reactive stress reacting to the shear stress,
the measuring step for measuring the complex viscosity modulus and the two complex elasticity moduli being based on the reactive stress;

3) a first operating step for operating the apparent activation energy of the viscoelastic material, the apparent activation energy being given by the following expression:

$$\eta^* = A \cdot \exp(Ea/RT)$$

where
   T is the temperature at the measuring step,
   R is a gas constant,
   $\eta^*$ is the complex viscosity modulus, and
   Ea is the apparent activation energy;

4) a second operating step for operating the complex elasticity modulus change ratio which is a ratio between the two complex elasticity moduli measured at the measuring step;

5) a first comparing step for making a following comparison, so as to judge the processability of the viscoelastic material:
   I) the apparent activation energy operated at the first operating step, compared with the processable range of the apparent activation energy which processable range is memorized at the memorizing step;

6) a second comparing step for making a following comparison, so as to judge the processability of the viscoelastic material:
   I) the complex elasticity modulus change ratio operated at the second operating step, compared with the processable range of the complex elasticity modulus change ratio which processable range is memorized at the memorizing step; and 7) a discharge operating step for operating a discharge of an extruder, the discharge being applicable to a processed part which is judged to be processable at the second comparing step, wherein,
the extruder is so controlled as to bring about the discharge operated at the discharge operating step, and
when the first comparing step and the second comparing step judge that the viscoelastic material is not processable, the mixing condition for the viscoelastic material is revised.

13. The method for controlling the processing operation of the viscoelastic material, as claimed in claim 12, wherein the method further comprises a developing step for developing in advance a datum of the complex elasticity modulus change ratio relative to a screw speed of the extruder, the discharge operating step operating the discharge referring to the datum developed at the developing step.

* * * * *